(12) United States Patent
Boling et al.

(10) Patent No.: US 8,712,552 B2
(45) Date of Patent: Apr. 29, 2014

(54) TREATMENT DEVICES WITH DELIVER-ACTIVATED INFLATABLE MEMBERS, AND ASSOCIATED SYSTEMS AND METHODS FOR TREATING THE SPINAL CORD AND OTHER TISSUES

(71) Applicant: Nevro Corporation, Menlo Park, CA (US)

(72) Inventors: C. Lance Boling, San Jose, CA (US); James Makous, Santa Clarita, WA (US)

(73) Assignee: Nevro Corporation, Menlo Park, CA (US)

( * ) Notice: Subject to any disclaimer, the term of this patent is extended or adjusted under 35 U.S.C. 154(b) by 0 days.

(21) Appl. No.: 13/678,435

(22) Filed: Nov. 15, 2012

(65) Prior Publication Data

US 2013/0144305 A1 Jun. 6, 2013

Related U.S. Application Data

(62) Division of application No. 12/104,230, filed on Apr. 16, 2008, now Pat. No. 8,326,439.

(51) Int. Cl.
*A61N 1/04* (2006.01)
*A61N 1/375* (2006.01)

(52) U.S. Cl.
USPC ............................................. 607/122

(58) Field of Classification Search
USPC .............................. 607/116, 117, 122
See application file for complete search history.

(56) References Cited

U.S. PATENT DOCUMENTS

| | | | |
|---|---|---|---|
| 3,738,368 A | 6/1973 | Avery et al. | |
| 4,136,703 A | 1/1979 | Wittkampf | |
| 4,282,886 A | 8/1981 | King | |
| 4,519,403 A | 5/1985 | Dickhudt | |
| 5,052,375 A | 10/1991 | Stark et al. | |
| 5,143,090 A | 9/1992 | Dutcher et al. | |
| 5,211,165 A | 5/1993 | Dumoulin et al. | |
| 5,251,634 A | 10/1993 | Weinberg | |
| 5,325,873 A | 7/1994 | Hirschi et al. | |
| 5,425,367 A | 6/1995 | Shapiro et al. | |
| 5,484,445 A | 1/1996 | Knuth et al. | |
| 5,527,358 A | 6/1996 | Mehmanesh et al. | |

(Continued)

FOREIGN PATENT DOCUMENTS

WO  WO-2008094952 A2  8/2008

OTHER PUBLICATIONS

International Search Report and Written Opinion, International Application No. PCT/US08/40700, Applicant: Nevro Corporation, mailed Jun. 9, 2009, 11 pages.

*Primary Examiner* — Tammie K Heller
(74) *Attorney, Agent, or Firm* — Perkins Coie LLP (57) ABSTRACT

The present application includes treatment systems having delivery-activated inflatable members, and associated systems and methods for treating the spinal cord and other tissues. A treatment system in accordance with one embodiment includes a lead body having an opening, an inner surface position around the opening, and an inflatable member carried by the lead body, with at least one of the inflatable member and the lead body including a frangible portion accessible from the opening. The inflatable member can have an expandable interior volume bounded at least in part by the frangible portion. The system can further include a delivery device received in the opening of the lead body and positioned to open a passage through the frangible portions between the interior volume of the inflatable member and the opening of the lead body when the delivery device is removed from the opening of the lead body.

20 Claims, 5 Drawing Sheets

(56) References Cited

U.S. PATENT DOCUMENTS

| | | |
|---|---|---|
| 5,549,555 A | 8/1996 | Sohn |
| 5,549,662 A | 8/1996 | Fordenbacher |
| 5,728,148 A | 3/1998 | Bostrom et al. |
| 5,741,319 A | 4/1998 | Woloszko et al. |
| 5,782,898 A | 7/1998 | Dahl et al. |
| 5,846,196 A | 12/1998 | Siekmeyer et al. |
| 5,964,730 A | 10/1999 | Williams et al. |
| 6,024,702 A | 2/2000 | Iversen |
| 6,038,480 A | 3/2000 | Hrdlicka et al. |
| 6,041,259 A | 3/2000 | Agarwala et al. |
| 6,132,561 A | 10/2000 | Mincher et al. |
| 6,161,047 A | 12/2000 | King et al. |
| 6,163,727 A | 12/2000 | Errico |
| 6,192,278 B1 | 2/2001 | Werner et al. |
| 6,205,361 B1 | 3/2001 | Kuzma et al. |
| 6,319,241 B1 | 11/2001 | King et al. |
| 6,325,778 B1 | 12/2001 | Zadno-Azizi et al. |
| 6,487,446 B1 | 11/2002 | Hill et al. |
| 6,510,347 B2 | 1/2003 | Borkan |
| 6,697,676 B2 | 2/2004 | Dahl et al. |
| 6,704,605 B2 | 3/2004 | Soltis et al. |
| 6,714,822 B2 | 3/2004 | King et al. |
| 6,746,474 B2 | 6/2004 | Saadat |
| 6,758,854 B1 | 7/2004 | Butler et al. |
| 6,795,737 B2 | 9/2004 | Gielen et al. |
| 6,832,115 B2 | 12/2004 | Borkan |
| 6,853,862 B1 | 2/2005 | Marchal et al. |
| 6,895,283 B2 | 5/2005 | Erickson et al. |
| 6,909,918 B2 | 6/2005 | Stypulkowski |
| 6,920,357 B2 | 7/2005 | Osorio et al. |
| 6,920,359 B2 | 7/2005 | Meadows et al. |
| 6,934,589 B2 | 8/2005 | Sundquist et al. |
| 6,944,501 B1 | 9/2005 | Pless |
| 6,961,621 B2 | 11/2005 | Krishnan et al. |
| 6,999,819 B2 | 2/2006 | Swoyer et al. |
| 7,054,690 B2 | 5/2006 | Imran |
| 7,099,718 B1 | 8/2006 | Thacker et al. |
| 7,177,702 B2 | 2/2007 | Wallace et al. |
| 7,182,783 B2 | 2/2007 | Trieu |
| 7,184,842 B2 | 2/2007 | Seifert et al. |
| 7,187,982 B2 | 3/2007 | Seifert et al. |
| 7,191,018 B2 | 3/2007 | Gielen et al. |
| 7,200,446 B2 | 4/2007 | Borkan |
| 7,276,057 B2 | 10/2007 | Gerber |
| 7,379,776 B1 | 5/2008 | Chitre et al. |
| 7,769,472 B2 | 8/2010 | Gerber |
| 7,797,054 B2 | 9/2010 | Skubitz et al. |
| 7,822,482 B2 | 10/2010 | Gerber |
| 7,856,277 B1 | 12/2010 | Thacker et al. |
| 7,983,766 B1 | 7/2011 | Thacker et al. |
| 7,996,055 B2 | 8/2011 | Hauck et al. |
| 8,092,456 B2 | 1/2012 | Bleich et al. |
| 8,128,600 B2 | 3/2012 | Gill |
| 8,326,439 B2 | 12/2012 | Boling et al. |
| 2001/0053885 A1 | 12/2001 | Gielen et al. |
| 2002/0019627 A1 | 2/2002 | Maguire et al. |
| 2002/0147486 A1 | 10/2002 | Soukup et al. |
| 2002/0156513 A1 | 10/2002 | Borkan |
| 2003/0062048 A1 | 4/2003 | Gradon et al. |
| 2003/0125786 A1 | 7/2003 | Gliner et al. |
| 2003/0136418 A1 | 7/2003 | Behm |
| 2004/0097803 A1 | 5/2004 | Panescu |
| 2005/0065588 A1 | 3/2005 | Zhao et al. |
| 2005/0075684 A1 | 4/2005 | Phillips et al. |
| 2005/0203599 A1 | 9/2005 | Garabedian et al. |
| 2006/0206183 A1 | 9/2006 | Pyles et al. |
| 2006/0247569 A1 | 11/2006 | Bertrand et al. |
| 2006/0259110 A1 | 11/2006 | Wallace et al. |
| 2006/0282121 A1 | 12/2006 | Payne et al. |
| 2006/0282123 A1 | 12/2006 | Hunter et al. |
| 2007/0027514 A1 | 2/2007 | Gerber |
| 2007/0027515 A1 | 2/2007 | Gerber |
| 2007/0106339 A1 | 5/2007 | Errico et al. |
| 2007/0135881 A1 | 6/2007 | Vilims |
| 2007/0167992 A1 | 7/2007 | Carley |
| 2007/0255365 A1 | 11/2007 | Gerber et al. |
| 2008/0027505 A1 | 1/2008 | Levin et al. |
| 2008/0046036 A1 | 2/2008 | King et al. |
| 2008/0103576 A1 | 5/2008 | Gerber |
| 2008/0103578 A1 | 5/2008 | Gerber |
| 2008/0103579 A1 | 5/2008 | Gerber |
| 2008/0103580 A1 | 5/2008 | Gerber |
| 2008/0140152 A1 | 6/2008 | Imran et al. |
| 2008/0183257 A1 | 7/2008 | Imran et al. |
| 2010/0292769 A1 | 11/2010 | Brounstein et al. |
| 2011/0029056 A1 | 2/2011 | Skubitz et al. |
| 2011/0031961 A1 | 2/2011 | Durand et al. |
| 2011/0166621 A1 | 7/2011 | Cowan et al. |
| 2011/0167630 A1 | 7/2011 | Heruth et al. |
| 2011/0184488 A1 | 7/2011 | De Ridder |
| 2011/0202097 A1 | 8/2011 | Bonde et al. |
| 2011/0224682 A1 | 9/2011 | Westlund et al. |
| 2011/0224710 A1 | 9/2011 | Bleich |
| 2011/0230943 A1 | 9/2011 | Johnson et al. |
| 2012/0083709 A1 | 4/2012 | Parker et al. |

TREATMENT DEVICES WITH DELIVER-ACTIVATED INFLATABLE MEMBERS, AND ASSOCIATED SYSTEMS AND METHODS FOR TREATING THE SPINAL CORD AND OTHER TISSUES

CROSS REFERENCE TO RELATED APPLICATION

This application is a divisional application of U.S. patent application Ser. No. 12/104,230, filed on Apr. 16, 2008, now U.S. Pat. No. 8,326,439 and entitled "TREATMENT DEVICES WITH DELIVERY-ACTIVATED INFLATABLE MEMBERS, AND ASSOCIATED SYSTEMS and METHODS FOR TREATING THE SPINAL CORD AND OTHER TISSUES," which is incorporated herein in its entirety by reference.

TECHNICAL FIELD

The present disclosure is directed generally to treatment devices with delivery-activated inflatable members, and associated systems and methods for treating the spinal cord and other tissues.

BACKGROUND

Neurological stimulators have been developed to treat pain, movement disorders, functional disorders, spasticity, cancer, cardiac disorders, and several other medical conditions. Implantable neurological stimulation systems generally have an implantable pulse generator and one or more electrode leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes. In many cases, the SCS leads are implanted percutaneously through a large needle inserted into the epidural space, with or without the assistance of a stylet. One concern of such leads is that the leads may not remain in the desired position after being implanted. This is undesirable because, if the leads migrate from the initial implantation site, the stimulation provided by the electrodes may no longer be directed to the appropriate target tissue. Accordingly, the efficacy of the treatment can be significantly compromised.

Another type of stimulation lead is a paddle lead. Paddle leads typically have a relatively flat body with electrodes arranged on one side of the body. Paddle leads are commonly used for cortical stimulation and SCS applications. Large paddle leads are desirable because they cover more neurological structures and, in at least some cases, may be more stable and less subject to migration than cylindrical leads. However, large paddle leads are not well suited to percutaneous implantation. As a result, large paddle leads are often surgically implanted using highly invasive procedures that are costly and can lead to patient complications.

DETAILED DESCRIPTION

A. Overview

Specific details of several embodiments of the disclosure are described below with reference to implantable leads for stimulating neural structures, methods for implanting leads, methods for manufacturing leads, and methods for stimulating a target neural site of a patient. Although selected embodiments are described below with respect to stimulating the dorsal root and/or neighboring regions of the spinal column to control pain, the leads may be used for stimulating the brain, peripheral neurological structures, and/or other tissue (e.g., muscle tissue). Several embodiments can have different configurations, components or procedures than those described in this section, and other embodiments may eliminate particular components or procedures. A person of ordinary skill in the relevant art, therefore, will understand that the invention may have other embodiments with additional elements, and/or may have other embodiments without several of the features shown and described below with reference to FIGS. 1-11.

A patient treatment system in accordance with a particular embodiment of the disclosure includes a lead body having an opening and an inner surface positioned around the opening. An inflatable member is carried by the lead body, and the inflatable member and/or the lead body include a frangible portion accessible from the opening. The inflatable member has an expandable interior volume bounded at least in part by the frangible portion. A delivery device is received in the opening of the lead body and is positioned to open a passage through the frangible portion between the interior volume of the inflatable member and the opening of the lead body when the delivery device is removed from the opening of the lead body. Accordingly, the delivery device can be used to position the lead body at the appropriate location in a patient and then, as the delivery device is removed from the lead body, it can open up communication between the inflatable member and the opening in the lead body. The inflatable member can be filled with a self-expanding material, so that it "automatically" inflates once the frangible portion has been broken. In another arrangement, a fluid can be driven into the inflatable member via the opening to inflate or further inflate the inflatable member. The lead body can have one or more electrical contacts that provide electrical stimulation to the patient, while the inflatable member secures or assists in securing the lead body at the appropriate patient location.

A representative method for positioning a lead in a patient includes percutaneously passing a lead into the patient's body while the lead is carried by a delivery device. The lead can have an inflatable volume, and the delivery device can be received in an opening of the lead. The method can further include forming a passage between the opening of the lead and the inflatable volume by at least partially removing the delivery device from the opening. The inflatable volume can then be expanded. In particular embodiments, forming the passage between the opening in the lead and the inflatable volume can include tearing a wall between the opening and the inflatable volume as the delivery device is removed. In a particular arrangement, an adhesive connection between the lead and the delivery device is broken as the delivery device is removed. In another embodiment, the delivery device can include a barb or other sharpened member that penetrates the wall between the opening in the lead and the inflatable volume as the delivery device is removed.

Yet another aspect of the disclosure includes a method for manufacturing a patient treatment device. A representative method includes positioning a delivery device proximate to a lead body and juxtaposing the delivery device and the lead body with the delivery device located within an opening of the lead body. The delivery device is positioned so that removing the delivery device from the opening forms a fluid passage between the opening and an interior volume of an expandable member carried by the lead body. The lead body can accordingly be adhered to the delivery device in one arrangement. The expandable member can be collapsed and/or evacuated prior to being attached to the delivery device, or it (along with an interior self-expanding material) can be collapsed around the delivery device while the delivery device is positioned within the lead body.

B. Embodiments of Implantable Neural Stimulation Systems and Associated Methods

Figure 1:
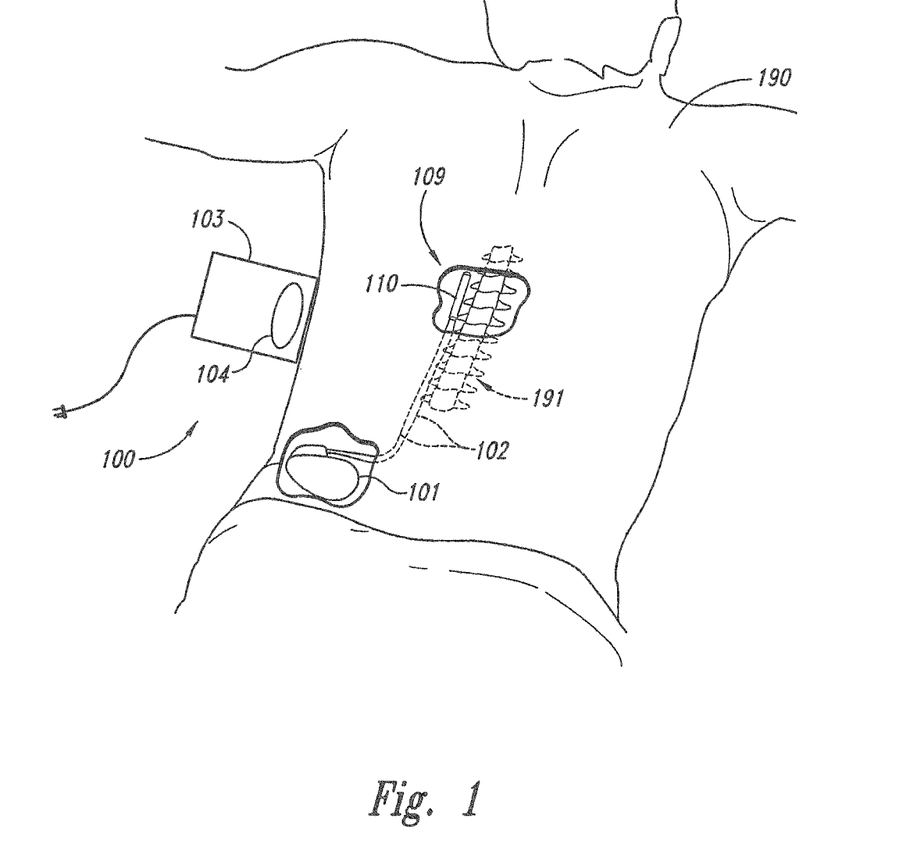
FIG. 1 is a schematic diagram of an implantable spinal stimulator with a lead body positioned at the spine in accordance with an embodiment of the present disclosure.

FIG. 1 schematically illustrates a representative treatment system 100 for providing relief from chronic pain and/or other conditions, arranged relative to the general anatomy of a patient's spinal cord 191. The system 100 can include a pulse generator 101 implanted subcutaneously within the patient 190 and coupled to a lead 109. The lead 109 can include a lead body 110 that carries features for delivering therapy to the patient 190 and resisting the ability of the lead body 110 to move relative to the patient 190 after implantation. The pulse generator 101 can be connected directly to the lead body 110 or it can be coupled to the lead body 110 via a communication link 102. As used herein, the term lead body includes any of a number of suitable substrates and/or support members that carry devices for providing therapy signals to the patient 190. For example, the lead body 110 can include one or more electrodes or electrical contacts that direct electrical signals into the patient's tissue to provide for patient relief. In other embodiments, the lead body 110 can carry other devices that direct electrical and/or other types of signals to the patient.

The pulse generator 101 can transmit signals to the lead body 110 that up-regulate (e.g., stimulate) and/or down-regulate (e.g., block) target nerves. Accordingly, the pulse generator 101 can include a computer-readable medium containing instructions for generating and transmitting suitable therapy signals. The pulse generator 101 and/or other elements of the system 100 can include one or more processors, memories, and/or input/output devices. The pulse generator 101 can include multiple portions, e.g., for directing signals in accordance with multiple signal delivery parameters, housed in a single housing (as shown in FIG. 1), or in multiple housings. Representative signal delivery parameters are disclosed in pending U.S. Provisional Application No. 60/985,353, filed Nov. 5, 2007, assigned to the assignee of the present application, and incorporated herein by reference.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In still further embodiments, an external programmer (not shown) can communicate with the implantable pulse generator 101 via electromagnetic induction. Accordingly, a practitioner can update the therapy instructions provided by the pulse generator 101. Optionally, the patient may also have control over at least some therapy functions, e.g., starting and/or stopping the pulse generator 101.

Figure 2:
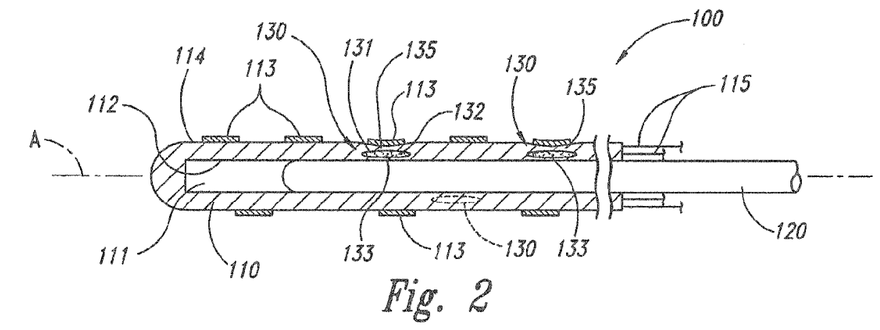
FIG. 2 is a partially schematic, cross-sectional side view of a lead body and delivery device configured in accordance with a particular embodiment of the disclosure.

FIG. 2 is a partially schematic, cross-sectional side view of a portion of the system 100 described above with reference to FIG. 1, including the lead body 110 temporarily carried by a delivery device 120. The lead body 110 can be elongated along an axis A and can have an opening 111 that receives the delivery device 120. The delivery device 120 can accordingly include a stylet, guidewire, and/or other suitable device that is releasably positioned within the opening 111. The lead body 110 can have a generally annular arrangement with an inner surface 112 bounding the opening 111, and an outer surface 114 facing outwardly from the inner surface 112. The lead body 110 can carry one or more electrodes 113 at the outer surface 114, and one or more wires 115 or other suitable links can provide a signal path by which therapy signals are directed from the pulse generator 101 (FIG. 1) to the electrodes or electrical contacts 113. The lead body 110 can be formed from any of a variety of known, suitable, biocompatible, and generally insulating materials, e.g., biocompatible plastics. The electrical contacts 113 can be formed from any of a variety of known, suitable, biocompatible and generally conductive materials, e.g., palladium, iridium, stainless steel, titanium or platinum.

The system 100 can further include one or more inflatable and/or expandable members 130 (two are shown in solid lines in FIG. 2 for purposes of illustration) carried by the lead body 110. The inflatable members 130 can be formed from a suitable, biocompatible, balloon-type material, and can be made integral with the lead body 110 or formed separately and attached to the lead body 110. The material forming the inflatable member 130 can be elastic in some embodiments and generally inelastic (though still flexible enough to collapse and expand) in others. Individual inflatable members 130 can include an interior volume 131 bounded at least in part by an outwardly facing exterior portion 135, and an inwardly facing frangible portion 133 that faces toward the delivery device 120. In some cases, the interior volume 131 can be empty and in other cases the interior volume 131 can be filled with a self-inflating material 132 (e.g., an open-cell foam or other suitable material). Suitable materials can include biocompatible foams that are generally similar in physical properties to the open-cell foams used in camping mattresses. In either of these embodiments, the interior volume 131 can have a collapsed state (shown in FIG. 2) and an expanded state (described further below with reference to FIGS. 5A and 5B). When the lead body 110 is carried by the delivery device 120 and placed percutaneously in the patient, the inflatable members 130 are generally collapsed to reduce the diameter of the lead body 110 and therefore ease its entry into the patient. The inflatable members 130 can be axially aligned with corresponding electrodes 113, as shown in solid lines in FIG. 2, and/or one or more inflatable members 130 can be axially offset from corresponding electrodes 113, as shown in dashed lines in FIG. 2.

Figure 3A:
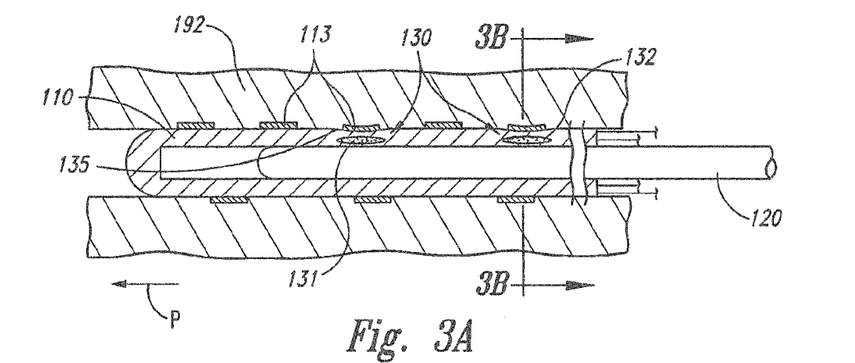
FIG. 3A is a partially schematic cross-sectional side view of the lead body shown in FIG. 2 implanted in patient tissue in accordance with a particular embodiment of the disclosure.

FIG. 3A schematically illustrates the lead body 110 and the delivery device 120 after both have been inserted as a unit into patient tissue 192. Arrow P indicates the insertion direction. As shown in FIG. 3A, the inflatable members 130 remain collapsed during this process.

Figure 3B:
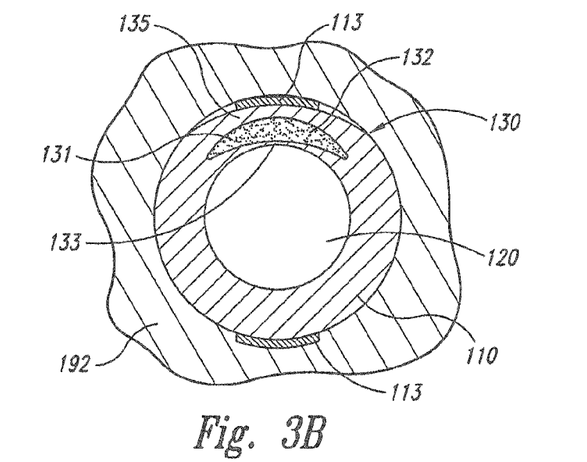
FIG. 3B is a partially schematic sectional view of the lead body taken substantially along line 3B-3B of FIG. 3A.

FIG. 3B is a partially schematic, sectional view of the delivery device 120 and the lead body 110, taken substantially along line 3B-3B of FIG. 3A. As shown in this view, the frangible portion 133 can be relatively thin and/or weak when compared to the exterior portion 135 of the inflatable member 130 located outwardly from the interior volume 131. In a particular arrangement, the frangible portion 133 can be the weakest portion of the inflatable member 130. In any of the foregoing embodiments, and as described further below, the frangible portion 133 can be positioned and configured to be broken, disrupted, penetrated, and/or otherwise opened as the delivery device 120 is withdrawn.

Figure 4:
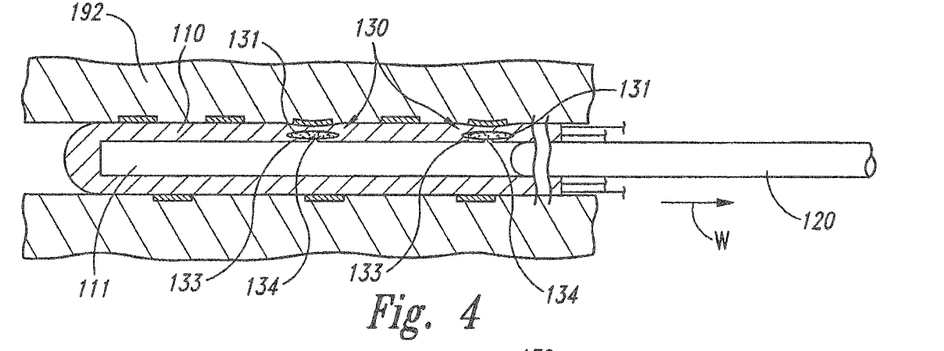
FIG. 4 is a partially schematic illustration of the lead body shown in FIG. 3A as an associated delivery device is withdrawn in accordance with a particular embodiment of the disclosure.

FIG. 4 is a cross-sectional illustration of the lead body 110 as the delivery device 120 is being withdrawn from the opening 111 in which is it received. During the withdrawal process, the practitioner can hold the proximal end of the lead body 110 (which, at this point, extends outside the patient's body) in place, while withdrawing the delivery device 120. As the delivery device 120 is withdrawn (indicated by arrow W), the action of withdrawing the delivery device 120 can open up passages 134 between individual interior volumes 131 and the central opening 111 in the lead body 110. For example, as will be discussed in greater detail later with reference to FIGS. 9-11, each of the frangible portions 133 may be attached to the delivery device 120 with a volume of adhesive material. As the delivery device 120 is withdrawn, the relative motion between the delivery device 120 and the lead body 110 tears an opening in the frangible portion 133, allowing for fluid communication between the opening 111 in the lead body 110 and the interior volumes 131 of individual inflatable members 130. The inflatable members 130 can then be inflated, expanded, and/or otherwise increased in size and/or changed in shape, as described below with reference to FIGS. 5A and 5B.

Figure 5A:
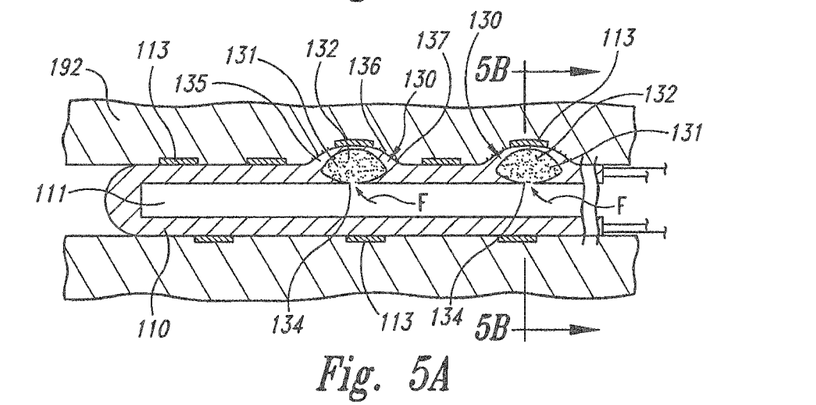
FIG. 5A is a partially schematic cross-sectional side view of the lead body shown in FIG. 4 after inflatable members have been inflated in accordance with a particular embodiment of the disclosure.

FIG. 5A is a side cross-sectional illustration of the lead body 110 after the delivery device 120 (FIG. 4) has been removed. The open passages 134 between the interior volumes 131 of individual inflatable members 130 and the opening 111 within the lead body 110 allow for a flow a fluid into the interior volumes 131, as indicated by arrows F. When the interior volumes 131 include a self-inflating material 132, the expansion of the self-inflating material 132 can draw fluid into the interior volumes 131 to further support the expanded shape of the inflatable members 130 shown in FIG. 5A. For example, if the opening 111 of the lead body 110 is in communication with bodily fluids in the patient tissue 192, such fluids can be drawn into the inflatable members 130 by the expanding action of the self-inflating material 132. In another embodiment, a practitioner can specifically direct fluids into the interior volumes 131 via the opening 111 in the lead body 110 and the passages 134. For example, the practitioner can direct a liquid, gas, foam, gel, or other flowable material into the interior volume 131 using a syringe or other suitable fluid delivery device. In a particular embodiment, the fluid directed into the inflatable members 130 can include an adhesive or other material that hardens once inside the inflatable members 130 to further solidify the expanded shape of the inflatable members 130. The fluid can be directed into the inflatable members 130 to supplement the action of the self-inflating material 132, or, (e.g., if the inflatable members 130 do not include a self-inflating material 132), the directed fluid alone can expand the inflatable members 130.

Figure 5B:
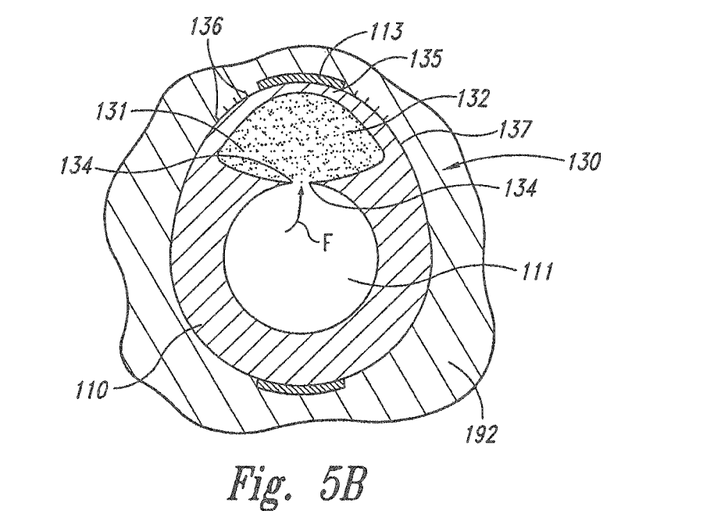
FIG. 5B is a partially schematic sectional view of the lead body taken substantially along line 5B-5B of FIG. 5A.

FIG. 5B is a partially schematic, sectional view of the lead body 110 taken substantially along line 5B-5B of FIG. 5A, and illustrates one of the inflatable members 130 in its inflated or otherwise expanded state. Referring to FIGS. 5A and 5B together, the inflatable members 130 in the expanded state can fix, secure, and/or otherwise at least partially restrict relative movement between the lead body 110 and the patient tissue 192 by projecting outwardly from the main contour of the lead body 110 and against the patient tissue 192. In a particular embodiment, the ability of the inflatable members 130 to secure the lead body 110 to the patient tissue 192 can be enhanced by roughness elements 136 positioned at an exterior surface 137 of the inflatable members 130. In other embodiments, the roughness elements 136 may be eliminated.

The degree (if any) to which the inflatable members 130 apply a force to the patient tissue 192 can be selected depending upon the characteristics of the particular implantation site. For example, if the inflatable members 130 carry electrodes 113 and are positioned so that the electrodes 113 contact target neural sites (e.g., neurons), then it may be desirable to arrange the inflatable members 130 so that the electrodes 113 touch and/or mate with the adjacent tissue, but do not apply a significant force to the adjacent tissue, so as to avoid creating a patient sensation and/or other potentially undesirable side effect. In another embodiment, for example, if the electrodes 113 are spaced apart from the inflatable members 130, the inflatable members 130 can apply some force to the tissue 192 to secure the lead body 110 in position. For example, if the inflatable members 130 bear against bony tissue or other tissue that is less sensitive than neural tissue, it may be acceptable to both patient and practitioner to have the inflatable members 130 apply some (e.g., low level) force to the tissue.

Figure 6:
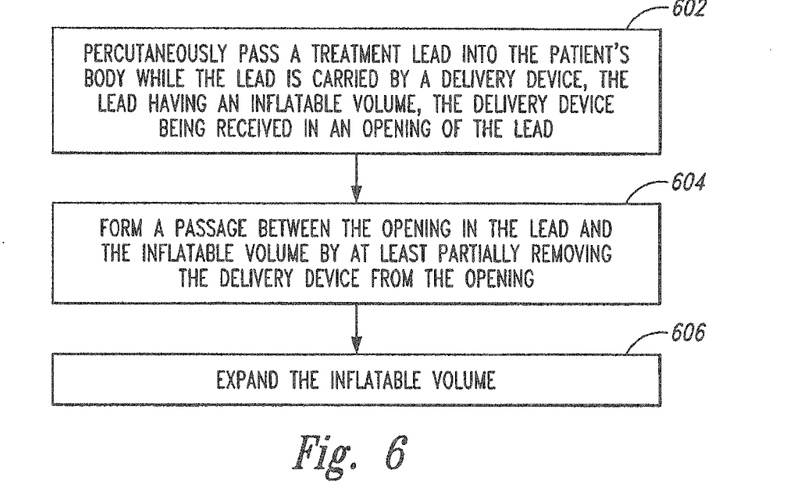
FIG. 6 is a flow diagram illustrating a process for positioning a delivery lead in accordance with a particular embodiment of the disclosure.

FIG. 6 is a flow diagram illustrating a process 600 for positioning a lead in a patient. The process 600 can include percutaneously passing a lead into the patient's body while the lead is carried by a delivery device (process portion 602). The lead includes an inflatable volume and the delivery device is received in an opening of the lead. Process portion 604 includes forming a passage between the opening in the lead and the inflatable volume by at least partially removing the delivery device from the opening. For example, the passage can be formed when an adhesive connection between the lead and the delivery device is broken or otherwise disturbed. In process portion 606, the inflatable volume is expanded, for example, via a self-inflating material and/or an actively delivered fluid. Once the lead is in place, the implantable pulse generator (FIG. 1) can be activated to deliver therapeutic signals to the patient via electrodes carried by the lead.

Figure 7:
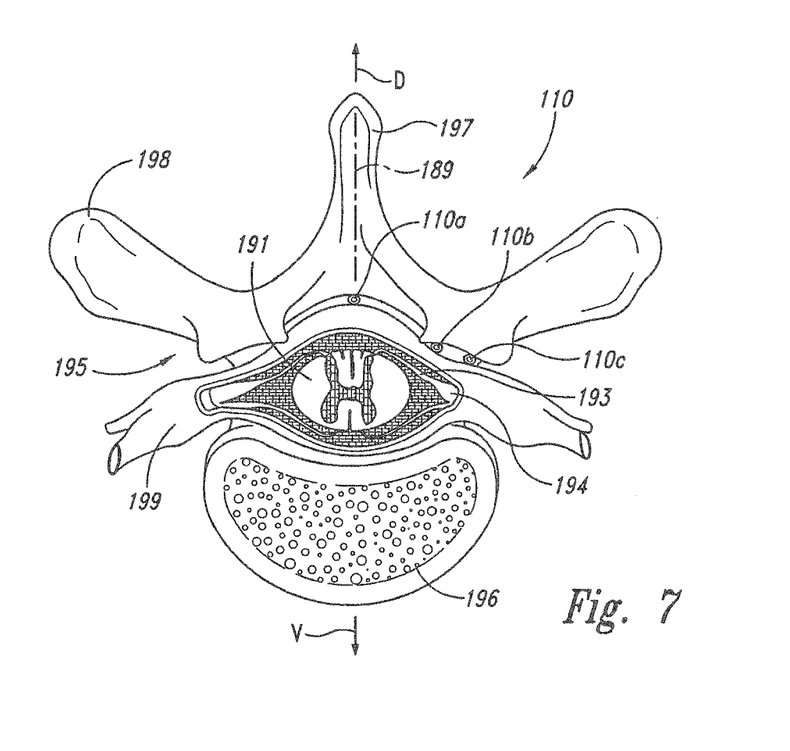
FIG. 7 is a cross-sectional illustration of the spinal cord and adjacent tissue, illustrating representative implantation locations for lead bodies in accordance with particular embodiments of the disclosure.

FIG. 7 is a cross-sectional illustration of the spinal cord 191 and an adjacent vertebra 195, along with selected representative locations for representative lead bodies 110 (shown as lead bodies 110a-110c) in accordance with several embodiments of the disclosure. The spinal cord 191 is located between a ventrally located vertebral body 196 and the dorsally located transverse process 198 and spinous process 197. Arrows V and D identify ventral and dorsal directions, respectively. The spinal cord itself 191 is located within the dura mater 199, which also surrounds portions of the nerves exiting the spinal cord 191, including the dorsal roots 193 and dorsal root ganglia 194. In a particular embodiment, a lead body 110a can be positioned centrally in a lateral direction (e.g., aligned with the spinal cord midline 189) to provide signals directly to the spinal cord 191. In other embodiments, the lead body can be located laterally from the midline 189. For example, the lead body can be positioned proximate to the dorsal root 193 (as indicated by lead body 110b) and/or proximate to the dorsal root ganglion 194 (as indicated by lead body 110c). Other suitable locations for the lead body 110 include the "gutter," also located laterally from the midline 189, and the dorsal root entry zone. In still further embodiments, the lead bodies may have other locations proximate to the spinal cord 191 and/or proximate to other target neural populations e.g., laterally from the midline 189 and medially from the dorsal root ganglion 194. In yet further embodiments, devices having any of the characteristics described herein may be used to direct signals (e.g., electrical current) to tissues outside the patient's nervous system.

Figure 8:
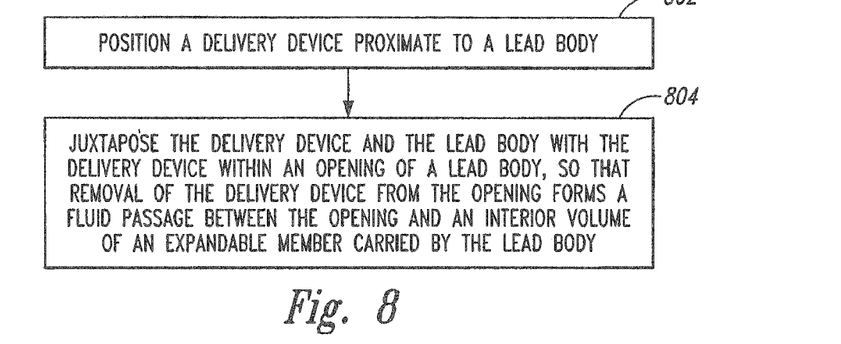
FIG. 8 is a flow diagram illustrating a method for manufacturing a patient treatment device in accordance with a particular embodiment of the disclosure.

FIG. 8 is a flow diagram illustrating a process 800 for manufacturing a treatment system in accordance with a particular embodiment. The process 800 can include positioning a delivery device proximate to a lead body (process portion 802) and juxtaposing the delivery device and the lead body with the delivery device located within an opening of the lead body (process portion 804). The delivery device and the lead body are juxtaposed so that removal of the delivery device form the opening forms a fluid passage between the opening and an interior volume of an expandable member carried by the lead body. Further details of representative processes are described below with reference to FIGS. 9-11.

Figure 9:
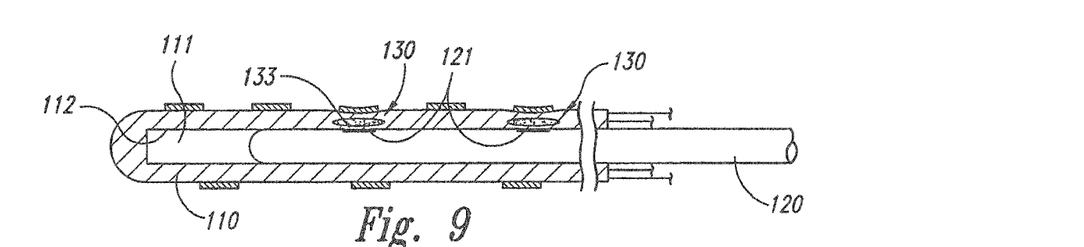
FIG. 9 is a partially schematic, cross-sectional side view of a lead body temporarily attached to a delivery device with an adhesive in accordance with a particular embodiment of the disclosure.

FIG. 9 illustrates the lead body 110 attached to the delivery device 120 with one or more adhesive volumes 121 (two are shown in FIG. 9), in accordance with a particular embodiment. In one aspect of this embodiment, the inflatable members 130 can be pre-evacuated so as to assume the collapsed shape shown in FIG. 9. With the inflatable members 130 in the collapsed configuration, the delivery device 120 can be inserted into the opening 111. The adhesive volumes 121 can be applied to the delivery device 120 and/or the lead body 110 prior to insertion. In a particular arrangement, the delivery device 120 can include recesses in which the adhesive volumes 121 are positioned, so as to avoid smearing the adhesive over the inner surface 112 of the lead body 110. In another embodiment, a recess can be located in the frangible portion 133 of the lead body 110, in addition to or in lieu of a recess located in the delivery device 120. In any of these embodiments, the adhesive volumes 121 can be allowed to set, cure or partially cure once the delivery device 120 is inserted to the desired location. When the lead body 110 and the delivery device 120 are inserted together into the patient, the adhesive volumes 121 can maintain the lead body 110 in a fixed position relative to the delivery device 120. When the delivery device 120 is then withdrawn, the adhesive volumes 121 can tear the frangible portions 133 and create the passages 134 described above. The inflatable members 130 then inflate, autonomously and/or via active fluid delivery, to secure or at least partially secure the lead body 110 in position.

Figure 10:
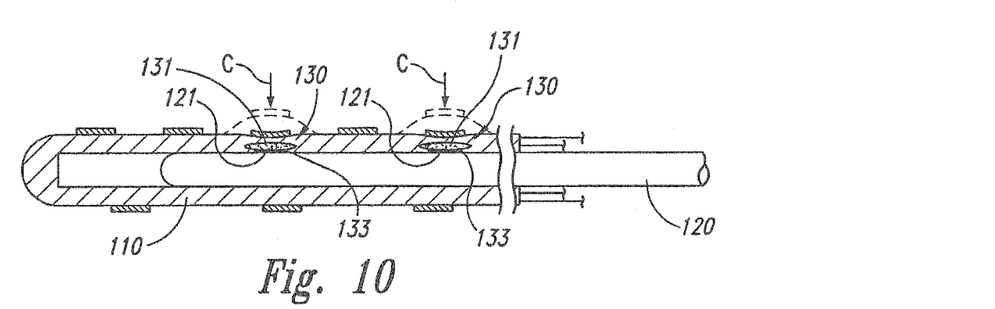
FIG. 10 is a partially schematic, cross-sectional side view of a lead body temporarily attached to a delivery device with an adhesive that forms a frangible portion in accordance with a particular embodiment of the disclosure.

FIG. 10 schematically illustrates another arrangement for temporarily attaching the lead body 110 to the delivery device 120. In this arrangement, the delivery device 120 can be inserted into the lead body 110 while the inflatable members 130 are in the inflated state, as indicated in dashed lines in FIG. 10. An adhesive 121 can be positioned at the appropriate locations on the delivery device 120 and/or the inflatable members 130 prior to insertion. When the lead body 110 has the correct axial position relative to the delivery device 120, the inflatable members 130 can be compressed, as indicated by arrows C to both collapse the inflatable members 130 and adhere the lead body 110 to the delivery device 120. The lead body 110 can then be percutaneously delivered into the patient, and the delivery device 120 can be withdrawn in a manner generally similar to that discussed above with reference to FIG. 9.

In one aspect of the arrangement described above with reference to FIG. 10, the inflatable members 130 include a pre-formed frangible portion 133, generally similar to the frangible portions shown in FIGS. 2-3B. In another embodiment, the adhesive 121 itself can form the frangible portion 133. In other words, the inflatable volumes 130 can initially have interior volumes 131 that open inwardly toward the delivery device 120. When the lead body 110 is attached to the delivery device 120, the adhesive 121 seals the interior volumes 131. When the delivery device 120 is later withdrawn (after the lead body 110 is implanted), the adhesive 121 disbands or otherwise fails, forming the passages that allow the inflatable volumes 130 to inflate.

Figure 11:
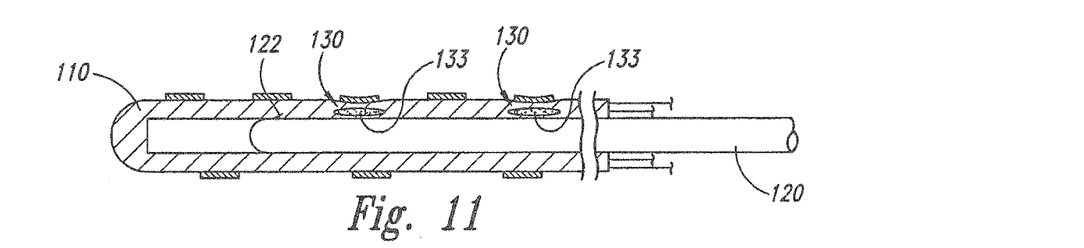
FIG. 11 is a partially schematic, cross-sectional side view of a delivery device having a barb for piercing the frangible portion of a lead body in accordance with another embodiment of the disclosure.

FIG. 11 illustrates still another embodiment in which the delivery device 120 includes a barb or other sharpened element 122 that can puncture, penetrate, and/or otherwise disturb the frangible portion 133. In one aspect of this embodiment, the delivery device 120 can be slid into the opening 111 in the lead body 110 from right to left, without the element 122 disturbing the frangible portions 133. Accordingly, the element can face proximally (e.g., to the right in FIG. 11). As the delivery device 120 is withdrawn from the lead body 110, the element 122 can puncture the frangible portions 133, allowing the inflatable members 130 to inflate and/or be inflated. The material of the lead body 110 can be thick enough to withstand any scoring that may be produced by the element 122 as it passes along other portions of the inner surface 112 (aside from the frangible portion 133), without compromising the integrity of the lead body 110. The element 122 can include one or more barbs, or other puncturing or hole-creating structures, e.g., a sharp-edged, rightward facing cup.

One feature of at least some of the foregoing embodiments is that the lead body can include one or more inflatable or otherwise expandable members having frangible portions that are opened as the associated delivery device is removed from the lead body. An advantage of this arrangement is that it can allow the inflatable member to have a collapsed (e.g., low-profile) shape as it is delivered into the patient's body, and an expanded shape (e.g., one that can secure the lead body in position) once the delivery tool has been removed. In particular embodiments, the inflatable member can assume the expanded shape automatically, e.g., when the inflatable member includes a self-inflating material and when the frangible portion is disrupted such that fluid can fill or at least partially fill the self-inflating material during inflation. This particular arrangement can reduce the number of tasks a practitioner performs when fixing or at least partially fixing the lead body in position in the patient's body. Another expected advantage of this particular arrangement is that the self-inflating material does not require continuous fluid pressure for the inflatable member to retain its expanded shape. Accordingly, the practitioner need not seal the inflatable member after it has expanded, and, if the inflatable member develops a leak (e.g., at its exterior surface), it can still retain its expanded shape.

From the foregoing, it will be appreciated that specific embodiments of the disclosure have been described herein for purposes of illustration, but that various modifications may be made without deviating form the disclosure. For example, the lead bodies may have arrangements other than those specifically shown and discussed above, including flatter or otherwise non-isodiametric cross-sectional shapes. As noted above, the lead body can be connected directly to an implanted pulse generator, or an additional signal communication link can be connected between the lead body and the implanted pulse generator. The lead body can include any of a variety of support structures that carry the appropriate signal delivery elements. Such elements can include electrical contacts, as discussed above, or other elements (e.g., ultrasonic or optical elements). Any of these elements may be carried by the inflatable member(s) and/or by other portions of the lead body. The inflatable members can extend around a portion of the perimeter of the lead body (as shown in FIGS. 3B and 5B) or around the entire perimeter at a given axial location. In other embodiments, one inflatable member at one axial location can have one circumferential position (e.g., centered at a 12:00 position) and another inflatable member can have another circumferential position (e.g., centered at a 6:00 position).

Certain aspects of the disclosure described in the context of particular embodiments may be combined or eliminated in other embodiments. For example, the barb or other sharpened element described above with reference to FIG. 11 may be combined with the adhesive described with reference to previous figures. Further, while advantages associated with certain embodiments have been described in the context of those embodiments, other embodiments may also exhibit such advantages, and not all embodiments need necessarily exhibit such advantages to fall within the scope of the invention. Accordingly, the disclosure can include other embodiments not expressly shown or described above.

We claim:

1. A method for positioning a treatment lead in a patient, comprising:

percutaneously passing a lead into the patient's body while the lead is carried by a delivery device, the lead including an inflatable volume having a self-expanding material therein, the delivery device being received in an opening of the lead; and forming a passage between the opening in the lead and the inflatable volume to expose and expand the self-expanding material by at least partially removing the delivery device from the opening.

2. The method of claim 1 wherein forming a passage includes tearing a wall between the opening in the lead and the inflatable volume by at least partially removing the delivery device from the opening.

3. The method of claim 1 wherein forming the passage includes allowing a flowable material into the opening and through the passage into the inflatable volume.

4. The method of claim 3 wherein forming the passage includes allowing a liquid into the inflatable volume.

5. The method of claim 3 wherein forming the passage includes allowing at least one of a gas, a foam, a liquid, a gel, and a curable material into the inflatable volume.

6. The method of claim 1 wherein forming a passage includes puncturing a material bounding the inflatable volume.

7. The method of claim 1 wherein forming a passage includes disrupting an adhesive between the lead and the delivery device.

8. The method of claim 1 wherein forming the passage between the opening in the lead and the inflatable volume to expose and expand the self-expanding material includes positioning the inflatable volume against adjacent tissue to at least restrict motion between the treatment lead and the tissue.

9. The method of claim 8 wherein positioning the inflatable volume against adjacent tissue includes positioning the inflatable volume against bone tissue.

10. The method of claim 8 wherein the inflatable volume carries an electrical contact, and wherein positioning the inflatable volume against the adjacent tissue includes positioning the electrical contact against the adjacent tissue.

11. The method of claim 1 wherein the lead body has an electrical contact, and wherein passing the lead into the patient's body includes positioning the electrical contact in electrical communication with neurons in a spinal cord region of the patient.

12. The method of claim 11 wherein the neurons include spinal cord neurons.

13. The method of claim 11 wherein the neurons include dorsal root neurons.

14. The method of claim 11 wherein passing the lead into the patient's body includes positioning the lead in a gutter along the spinal cord.

15. The method of claim 11 wherein passing the lead into the patient's body includes positioning the lead in a dorsal root entry zone.

16. The method of claim 1 wherein the lead includes an electrical contact positioned adjacent to the inflatable volume, and wherein forming the passage between the opening in the lead and the inflatable volume to expose and expand the self-expanding material includes moving the electrical contact toward a target neural site.

17. The method of claim 1 wherein the lead includes an electrical contact, wherein the method further comprises positioning the electrical contact adjacent to neurons in a spinal cord region of the patient, and wherein forming the passage between the opening in the lead and the inflatable volume to expose and expand the self-expanding material includes expanding the inflatable volume to move the electrical contact toward the neurons.

18. The method of claim 1, further comprising expanding the inflatable volume via the self-expanding material to move an electrode carried by the lead toward a target neural site.

19. The method of claim 1, further comprising moving an electrical contact attached to the lead toward neurons in a spinal cord region of the patient via the expansion of the self-expanding material.

20. The method of claim 1, further comprising urging an electrode carried by the lead toward a target neural site via the expansion of the self-expanding material.

* * * * *